(12) United States Patent
Nakai et al.

(10) Patent No.: US 7,123,952 B2
(45) Date of Patent: *Oct. 17, 2006

(54) CARDIAC MAGNETIC FIELD DIAGNOZER FOR ATRIAL FLUTTER AND ATRIAL FIBRILLATION AND METHOD FOR IDENTIFYING ELECTRIC TURNING PATH OF ATRIAL FLUTTER AND ATRIAL FIBRILLATION

(75) Inventors: Kenji Nakai, Morioka (JP); Masahito Yoshizawa, Morioka (JP); Kohei Kawazoe, Morioka (JP); Keita Yamazaki, Inzai (JP); Satoshi Fujita, Osaka (JP); Itsuro Tamura, Osaka (JP)

(73) Assignees: Japan Science and Technology Corporation, Saitama (JP); Takenaka Corporation, Osaka (JP)

( * ) Notice: Subject to any disclaimer, the term of this patent is extended or adjusted under 35 U.S.C. 154(b) by 344 days.

This patent is subject to a terminal disclaimer.

(21) Appl. No.: 10/333,023

(22) PCT Filed: Jul. 17, 2001

(86) PCT No.: PCT/JP01/06192

§ 371 (c)(1),
(2), (4) Date: Oct. 14, 2003

(87) PCT Pub. No.: WO02/05713

PCT Pub. Date: Jan. 24, 2002

(65) Prior Publication Data

US 2004/0077964 A1    Apr. 22, 2004

(30) Foreign Application Priority Data

Jul. 18, 2000   (JP) ............................. 2001-217833

(51) Int. Cl.
*A61B 5/04* (2006.01)

(52) U.S. Cl. ..................................................... 600/509
(58) Field of Classification Search ......... 600/407–525
See application file for complete search history.

(56) References Cited

U.S. PATENT DOCUMENTS 6,941,165 B1 * 9/2005 Nakai et al. ................ 600/509

FOREIGN PATENT DOCUMENTS

EP        0968683 A1    1/2000

(Continued)

OTHER PUBLICATIONS

Robinson, S. E. et al., "Functional Neuroimaging by Synthetic Aperture Magnetometry (SAM)," Proceedings of the 11th International Conference on Biomagnetism, "Recent Advances in Biomagnetism," Tohoku University Press, 1999, pp. 302-305.
Hara, K. et al., "Science of Cerebric Magnetic Field —SQUID Measurement and Medical Applications," Ohmsha, Jan. 25, 1997, pp. 117-119 (with partial translation).

(Continued)

*Primary Examiner*—Scott M. Getzow
(74) *Attorney, Agent, or Firm*—Birch, Stewart, Kolasch & Birch, LLP

(57) ABSTRACT

A magnetic field distribution measurement device (1) provides a non-contact magnetic field measurement on a subject's chest at a plurality of coordinates and forms therefrom time-series magnetic field distribution data. A first arithmetic device (2) in response generates image data representing a three-dimensional, intramyocardial current density distribution. A second arithmetic device (3) receives a plurality of tomographic image data separately obtained by a tomographic diagnosis apparatus and processes the data to generate three-dimensional, anatomical image data. A display device (4) receives these data and displays on an anatomical image an image representing an intramyocardial current density. This can facilitate identifying an anatomical, positional relationship of an abnormal, electrical reentry circuit caused in heart muscle. Furthermore, the anatomical image may be replaced with an image representing a normal stimulation propagation circuit and serving as a template.

6 Claims, 15 Drawing Sheets

FOREIGN PATENT DOCUMENTS

| | | | |
|---|---|---|---|
| JP | 8-289877 | A | 11/1996 |
| JP | 10-276998 | A | 10/1998 |
| JP | 10-323335 | A | 12/1998 |
| JP | 11-128191 | A | 5/1999 |
| JP | 11-128224 | A | 5/1999 |
| JP | 2002-500909 | A | 1/2002 |
| WO | WO 98/15226 | A1 | 4/1998 |
| WO | WO-99/37206 | A1 | 7/1999 |

OTHER PUBLICATIONS

Ueda, T. et al., "Visualization of Source Current Distribution in Human Heart based on Magnetocardiogram Data," $9^{th}$ Digital Signal Processing Symposium, Nov. 10-11, 1994, pp. 307-312.

* cited by examiner

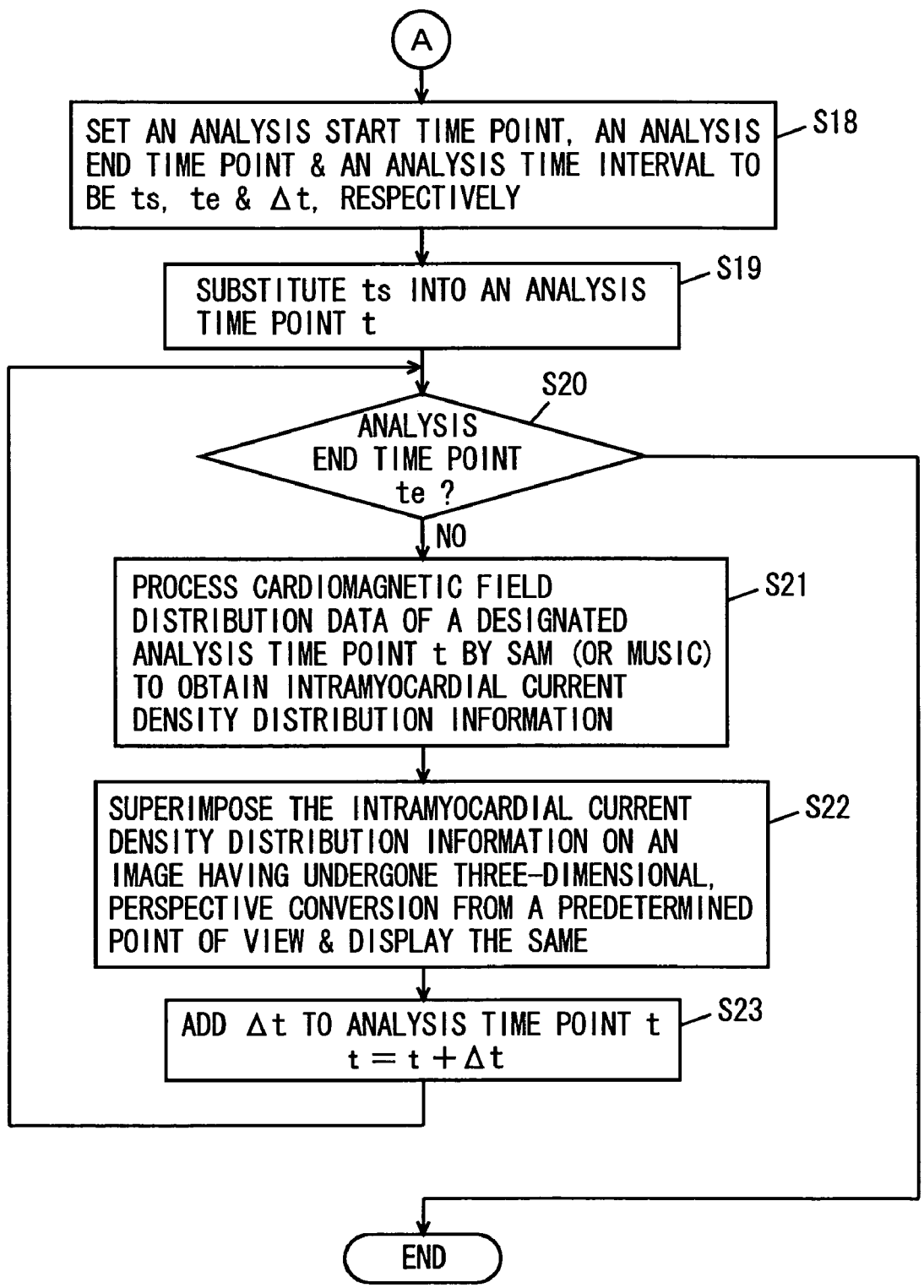

CARDIAC MAGNETIC FIELD DIAGNOZER FOR ATRIAL FLUTTER AND ATRIAL FIBRILLATION AND METHOD FOR IDENTIFYING ELECTRIC TURNING PATH OF ATRIAL FLUTTER AND ATRIAL FIBRILLATION

This application is the national phase under 35 U.S.C. § 371 of PCT International Application No. PCT/JP01/06192 which has an International filing date of Jul. 17, 2001, which designated the United States of America.

TECHNICAL FIELD

The present invention relates generally to magnetocardiographic diagnosis apparatuses and methods of identifying an electrical reentry circuit, and particularly to those employing non-contact magnetic field measurement to non-invasively diagnose a three-dimensional location of an abnormal, intramyocardial excitation propagation circuit causing atrial flutter and fibrillation.

BACKGROUND ART

Conventionally, recording electrocardiograms has been generally adopted as a technique to diagnose heart diseases.

However, conventional electrocardiography is insufficient for example to determine the location, size and geometry of a part to be treated in a heart surgery and it cannot satisfactorily locate an affected part.

This is attributed to the fact that electrocardiography is an indirect measurement methodology. Different subjects have different tissues existing between their hearts and body surfaces, different positional relationships between their hearts and other organs and bones, their respective hearts having different sizes, a different electric conductance for each tissue of their bodies, and the like. As such, it has been significantly difficult to accurately determine an affected part from information obtained from indirect measurement such as electrocardiography.

As such an indirect measurement methodology is disadvantageous, as described above, a method has been adopted to more directly identify the location of an affected part.

For example, thoracotomy is employed to expose a heart and a needle electrode is directly stabbed in the heart or a meshed electrode is brought into contact with the heart to measure myocardial potential at multiple points simultaneously to precisely locate an affected part. Thoracotomy, however, is a significant burden on patients. In addition, the multi-point, simultaneous, myocardial potential measurement and its data analysis effected in thoracotomy to identify the location of an affected part require a long period of time and thus prolong thoracotomy disadvantageously.

Accordingly there is a strong demand for a method capable of locating an affected part in a short period of time with high precision.

Another direct approach has also been adopted in recent years. It uses a catheter to conduct diagnosis and provide treatment. More specifically, a tip provided catheter having an electrode and a heater is inserted to intracardiac cavity and chest x-ray fluoroscopy is provided, while an electrophysiological test is conducted to locate an affected part and a methodology referred to as high frequency catheter cauterization is also employed to rapidly ablate a targeted site to rapidly treat the site.

In this approach, however, the electrophysiological test requires a period of time and chest x-ray fluoroscopy exposes doctors and radiographers to large doses of x-ray radiation.

It has been known that of various heart diseases, atrial flutter and atrial fibrillation are caused by an abnormal excitation propagation circuit formed in a heart muscle. More specifically, atrial flutter is caused by an abnormal, electrical reentry circuit, referred to as a macro reentry circuit, formed in a vicinity of a tricuspid annulus and atrial fibrillation is caused by an abnormal, electrical reentry circuit, referred to as a micro reentry circuit, formed in an atrium in large numbers (multiple wavelength theory). From a recent study it has been known that an early stage of paroxysmal atrial fibrillation would be induced by firing at a focus of a pulmonary vein.

To treat atrial flutter and fibrillation it is important to identify these reentry circuits and a firing site at a focus of a pulmonary vein. However, indirect measurement using electrocardiography, as described above, would hardly provide precise identification, and a myocardial potential measurement in thoracotomy and an electrophysiological test using a catheter or any other similar direct tests are a significant burden on patients and doctors.

Accordingly there is a strong demand for non-invasively diagnosing these reentry circuits and a firing part at a focus of a pulmonary vein.

In a variety of fields a superconducting quantum interference device (SQUID) magnetometer has been applied. It uses an SQUID capable of detecting with high sensitivity a magnetic flux of one billionth of geomagnetic field. In particular, in the field of somatometry, which strongly demands non-invasive measurement, as described above, an attempt is being made to use a SQUID magnetometer to provide a non-contact magnetic field measurement of human bodies.

In particular, the development of thin-film device fabrication technology in recent years has allowed the development of a DC-SQUID, and an attempt is being made to use a SQUID magnetometer to measure a magnetocardiogram, a distribution of a magnetic field of a heart.

However, a magnetocardiogram alone cannot directly display the location, size and geometry of an affected part in a human body and would hardly let a doctor know a correct, relative positional relationship of an electrical reentry circuit in a heart.

Accordingly it has been proposed that in diagnosing atrial flutter and fibrillation, the location of an abnormal, intramyocardial excitation propagation circuit causing atrial flutter and fibrillation is identified by visualizing an intramyocardial, electric current behavior from a magnetocardiographic distribution represented in a magnetocardiogram. One such approach adopted is to use one or more current dipoles to mimic the source of a magnetic field for visualization. If a large number of micro reentry circuits exist, however, the number of the circuits and their respective locations cannot accurately be identified. Furthermore in such an approach a result of mimicking the source of a magnetic filed would disadvantageously depend on an initial value that is set.

Accordingly the present invention contemplates a magnetocardiographic diagnosis apparatus for diagnosis of atrial flutter and fibrillation and a method of identifying the electrical reentry circuit, capable of employing non-invasive magnetic field measurement to obtain data representative of a three-dimensional, intramyocardial electrical behavior used to identify a positional relationship of an abnormal, intramyocardial electrical reentry circuit safely, rapidly and with high precision.

DISCLOSURE OF THE INVENTION

In accordance with the present invention a magnetocardiographic diagnosis apparatus for atrial flutter and fibrillation includes a magnetic field distribution measurement device, a first arithmetic device, a second arithmetic device and a display device. The magnetic field distribution measurement device performs a non-contact magnetic field measurement on a subject's chest at a plurality of coordinates to obtain a plurality of time-series magnetic field data corresponding to the plurality of coordinates, and also using the plurality of time-series magnetic field data to generate time-series magnetic field distribution data on the chest. The first arithmetic device uses the generated time-series magnetic field distribution data to generate data representative of a three-dimensional, intramyocardial, electrical behavior of the subject. The second arithmetic device processes separately provided, tomographic, thoracic data of the subject to generate data representative of an anatomical image. The display device displays an image of the three-dimensional, intramyocardial, electrical behavior represented by the data generated by the first arithmetic device, as superimposed on the anatomical image represented by the data generated by the second arithmetic device. Thus an abnormal, intramyocardial, electrical reentry circuit can be identified three-dimensionally.

Preferably the data generated by the first arithmetic device and representative of the three-dimensional, intramyocardial, electrical behavior is intramyocardial, time-series current density distribution data and the display device three-dimensionally displays a location of a plurality of abnormal, electrical reentry circuits on the anatomical image, as based on the time-series current density distribution data.

In accordance with the present invention in another aspect a magnetocardiographic diagnosis apparatus for atrial flutter and fibrillation includes a magnetic field distribution measurement device, an arithmetic device and a display device. The magnetic field distribution measurement device performs a non-contact magnetic field measurement on a subject's chest at a plurality of coordinates to obtain a plurality of time-series magnetic field data corresponding to the plurality of coordinates, and also using the plurality of time-series magnetic field data to generate time-series magnetic field distribution data on the chest. The arithmetic device uses the generated time-series magnetic field distribution data to generate data representative of a three-dimensional, intramyocardial, electrical behavior of the subject. The display device uses the data generated by the arithmetic device to superimpose together an image representing a stimulation propagation path of the subject extending from a sinoatrial node to a bundle of His and a Purkinje fiber network and an image representing an abnormal, intramyocardial, electrical reentry circuit and display the images. An abnormal, intramyocardial, electrical reentry circuit can thus be identified three-dimensionally.

Preferably the data generated by the arithmetic device and representative of the three-dimensional, intramyocardial, electrical behavior is intramyocardial, time-series current density distribution data and the display device three-dimensionally displays a location of a plurality of abnormal, electrical reentry circuits on the image of the stimulation propagation path, as based on the time-series current density distribution data.

In accordance with the present invention in another aspect a method of identifying an electrical reentry circuit for atrial flutter and fibrillation includes the steps of: performing a non-contact magnetic field measurement on a subject's chest at a plurality of coordinates to obtain a plurality of time-series magnetic field data corresponding to the plurality of coordinates and used to generate time-series magnetic field distribution data of the chest and generating first data representative of a three-dimensional, intramyocardial, electrical behavior of the subject from the generated time-series magnetic field distribution data; processing separately fed, tomographic, thoracic image data of the subject to generate second data representative of an anatomical image; and displaying an image of the three-dimensional, intramyocardial, electrical behavior represented by the first data, as superimposed on the anatomical image represented by the second data, to permit an abnormal, intramyocardial, electrical reentry circuit to be three-dimensionally identified.

Preferably the three-dimensional, intramyocardial, electrical behavior represented by the first data is an intramyocardial current density distribution.

In accordance with the present invention in still another aspect a method of identifying an electrical reentry circuit for atrial flutter and fibrillation includes the steps of: performing a non-contact magnetic field measurement on a subject's chest at a plurality of coordinates to obtain a plurality of time-series magnetic field data corresponding to the plurality of coordinates and used to generate time-series magnetic field distribution data of the chest and generating first data representative of a three-dimensional, intramyocardial, electrical behavior of the subject from the generated time-series magnetic field distribution data; and using the generated data to superimpose together an image representing a stimulation propagation path of the subject extending from a sinoatrial node to a bundle of His and a Purkinje fiber network and an image representing an abnormal, intramyocardial, electrical reentry circuit, and thus displaying the images to allow the abnormal, intramyocardial, electrical reentry circuit to be three-dimensionally identified.

Preferably the three-dimensional, intramyocardial, electrical behavior represented by the data is an intramyocardial current density distribution.

Thus in accordance with the present invention an image representing a three-dimensional, intramyocardial, electrical behavior obtained through a non-invasive magnetic field measurement that is superimposed on an anatomical image obtained by processing tomographic, thoracic image data of the same subject undergoing tomography with a separate, medical diagnosis apparatus can be displayed to allow doctors to identify safely, rapidly and with high precision the positional relationship relative to heart muscle of an abnormal, electrical reentry circuit causing atrial flutter and fibrillation.

Furthermore in accordance with the present invention an image representing a three-dimensional, intramyocardial, electrical behavior obtained through a non-invasive magnetic field measurement that is superimposed on an image representing a stimulation propagation path of the same subject extending from an atrioventricular node to a bundle of His-a Purkinje fiber network can be displayed to allow doctors to identify safely, rapidly and with high precision the positional relationship relative to heart muscle of an abnormal, electrical reentry circuit causing atrial flutter and fibrillation.

BRIEF DESCRIPTION OF THE DRAWINGS

In the drawings:

FIGS. 14 and 15 are a flow chart for illustrating an operation of the magnetocardiographic diagnosis apparatus of the second embodiment.

BEST MODE FOR CARRYING OUT THE INVENTION

Figure 1:
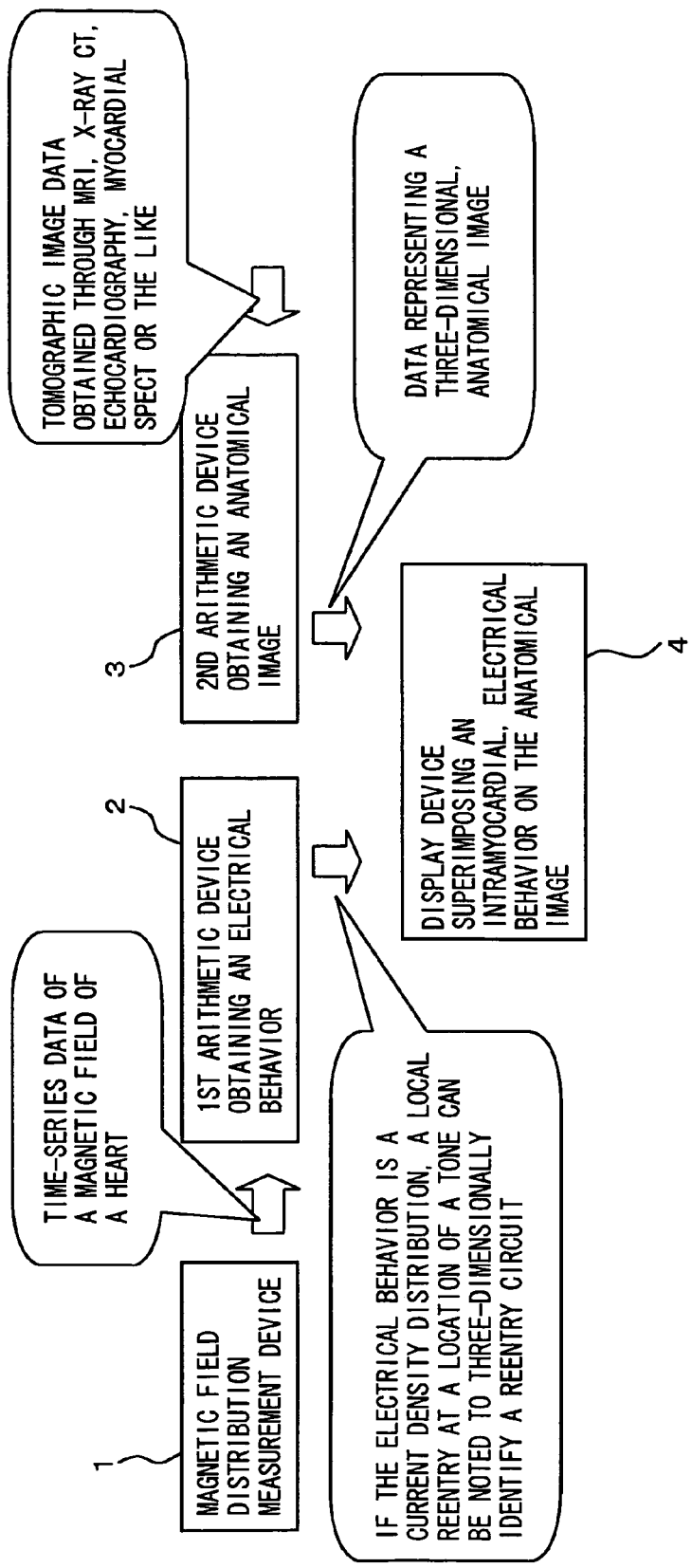
FIG. 1 is a functional block diagram schematically showing a configuration of a magnetocardiographic diagnosis apparatus for atrial flutter and fibrillation in accordance with the present invention in a first embodiment.

Hereinafter, the present invention in embodiments will specifically be described with reference to the drawings. Note that in the figures, like components are denoted by like reference characters and their descriptions will not be repeated.

First Embodiment

FIG. 1 is a functional block diagram schematically showing a configuration of a magnetocardiographic diagnosis apparatus for atrial flutter and fibrillation in accordance with the present invention in a first embodiment.

As shown in FIG. 1, a magnetic field distribution measurement device 1 for example uses a measurement means such as a SQUID magnetometer, as will be described hereinafter more specifically, to provide a non-contact magnetic field measurement on a subject's chest at a plurality of coordinates to obtain a plurality of time-series magnetic field data corresponding to the plurality of coordinates. The plurality of time-series magnetic field data are then used to generate and output time-series magnetic field distribution data of a magnetic field existing on the subject's chest, i.e., of the subject's heart.

The cardiac, time-series magnetic field distribution data provided by magnetic field distribution measurement device 1 is used by a first arithmetic device 2 for example employing a variety of known calculation methodologies, described hereinafter, to generate and output first data representing a three-dimensional, intramyocardial electrical behavior.

Furthermore, magnetic resonance imaging (MRI), x-ray, computed tomography (CT), echocardiography, myocardial single photon emission computed tomography (SPECT) or any other similar tomographic diagnosis apparatus is used to separately obtain tomographic, thoracic image data (including data of a plurality of tomographic images) of the same subject. The data are fed to a second arithmetic device 3 and processed thereby to generate and output second data representing a three-dimensional, anatomical image.

Note that when the first data is represented in an image and if the first arithmetic device 2 obtains an electrical behavior for example corresponding to an intramyocardial current density distribution then noting a local reentry of a tone of an image representing a current density distribution allows three-dimensional identification of an electrical reentry circuit.

Display device 4 superimposes an image representing a three-dimensional, intramyocardial electrical behavior (e.g., a current density distribution) represented by the first data generated by the first arithmetic device, on a three-dimensional, anatomical image of a subject's chest that is represented by the second data generated by the second arithmetic device 3, and displays the same. As a result on an anatomical image an intramyocardial, electrical reentry circuit's positional relationship can be identified three-dimensionally.

Figure 2:
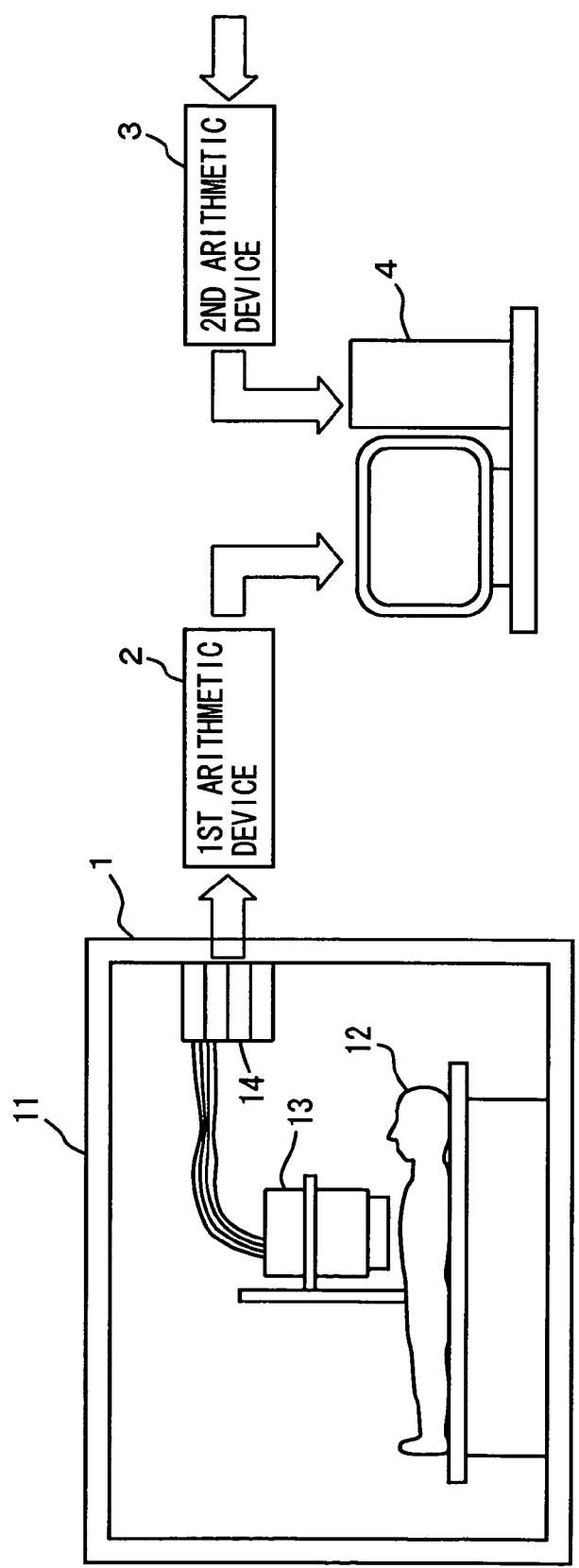
FIG. 2 is a block diagram more specifically showing the configuration of the FIG. 1 apparatus.

FIG. 2 is a block diagram more specifically showing the configuration of the magnetocardiographic diagnosis apparatus of the first embodiment shown in FIG. 1.

As shown in FIG. 2, magnetic field distribution measurement device 1 includes in a magnetic shield room (MSR) 11 a Dewar structure 13 incorporating a SQUID magnetometer and arranged on the chest of a subject 12 to provide a non-contact magnetic field measurement, and a magnetic field distribution data operation unit 14.

In Dewar structure 13 is provided a low-temperature environment filled with liquid helium to provide superconductance, and in the environment is accommodated a SQUID magnetometer configured of a detector coil formed of superconductor.

Figure 3:
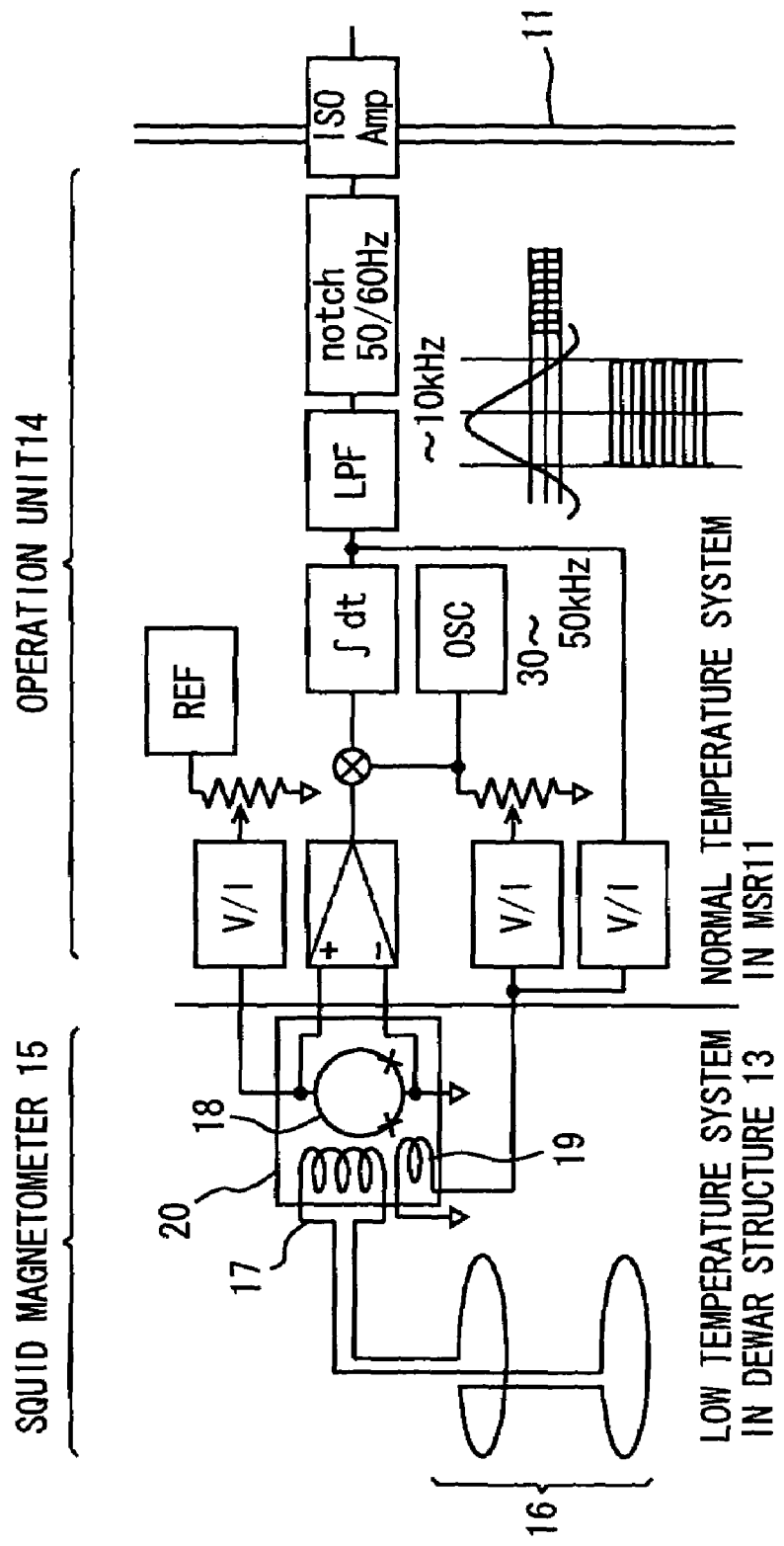
FIG. 3 is a block diagram showing a specific configuration of the magnetic field distribution measurement device shown in FIG. 2.

FIG. 3 is a block diagram more specifically showing a SQUID magnetometer 15 arranged in an ultra low temperature system provided in Dewar structure 13 arranged in MSR 11 shown in FIG. 2, and operation unit 14 arranged in MSR 11 of a normal temperature system.

Note that the configuration shown in FIG. 3 is that for a single channel for measuring magnetic field data of a single point on a subject's chest. As will be described hereinafter, in the present invention, on a subject's chest at a plurality of coordinates a magnetic field is measured, i.e., a multi-point, simultaneous magnetic field measurement is provided. Accordingly, MSR 11 of FIG. 2 would have therein the 1-channel configuration of FIG. 3 for each of channels required for a measurement.

With reference to FIG. 3, for a single channel a SQUID magnetometer generates magnetic field data, as described hereinafter.

SQUID magnetometer 15 includes a pickup coil 16 formed of superconductor for detecting a magnetic field generated from a surface of the chest of a subject. When pickup coil 16 captures a magnetic field, a current flows and drawn in by a coil 17 to create a magnetic field in an Nb shield 20.

Consequently, a magnetic field varying linearly relative to that created in Nb shield 20 is formed in a superconducting loop 18. Voltages of opposite ends of superconducting loop 18 are detected by an amplifier of operation unit 14 provided in MSR 11 of the normal temperature system. Operation unit 14 adjusts a current flowing through a modulation coil 19 provided in Nb shield 20 so that a detected voltage can thus be free of variation.

More specifically, the detection of an electric field of a human body by a SQUID is not a direct measurement of a magnetic field generated. Rather, a so-called a zeropotential method is used to provide a feedback to allow a magnetic field in superconducting loop 18 to have a constant value (more specifically, a current flowing through modulation coil 19 is adjusted to control a magnetic field generated in modulation coil 19 so that superconducting loop 18 internally, constantly has a constant magnetic field) to allow operation unit 14 to convert to an electrical signal a magnetic field detected at pickup coil 16 and output the signal. Such a feedback technique is typically a well known technique referred to as a flux locked loop (FLL).

Such a SQUID magnetometer 15 and its operation unit 14 are well known and will not further be described.

As has been described previously, the configuration shown in FIG. 3 is that necessary for measuring magnetic field data for a single channel and outputs an electrical signal corresponding to time-series magnetic field data of a magnetic field measured on a front side of the chest of a subject at a single point.

In the present invention, as has been described previously, a large number of sensors (SQUID magnetometers) are arranged on a front side of the chest of a subject to measure a magnetic field on the front side at multiple points. A magnetic field varies with time and for example even during a period corresponding to a single heart beat a magnetic field that is measured at different sites exhibits different variations depending on the sites.

Figure 4:
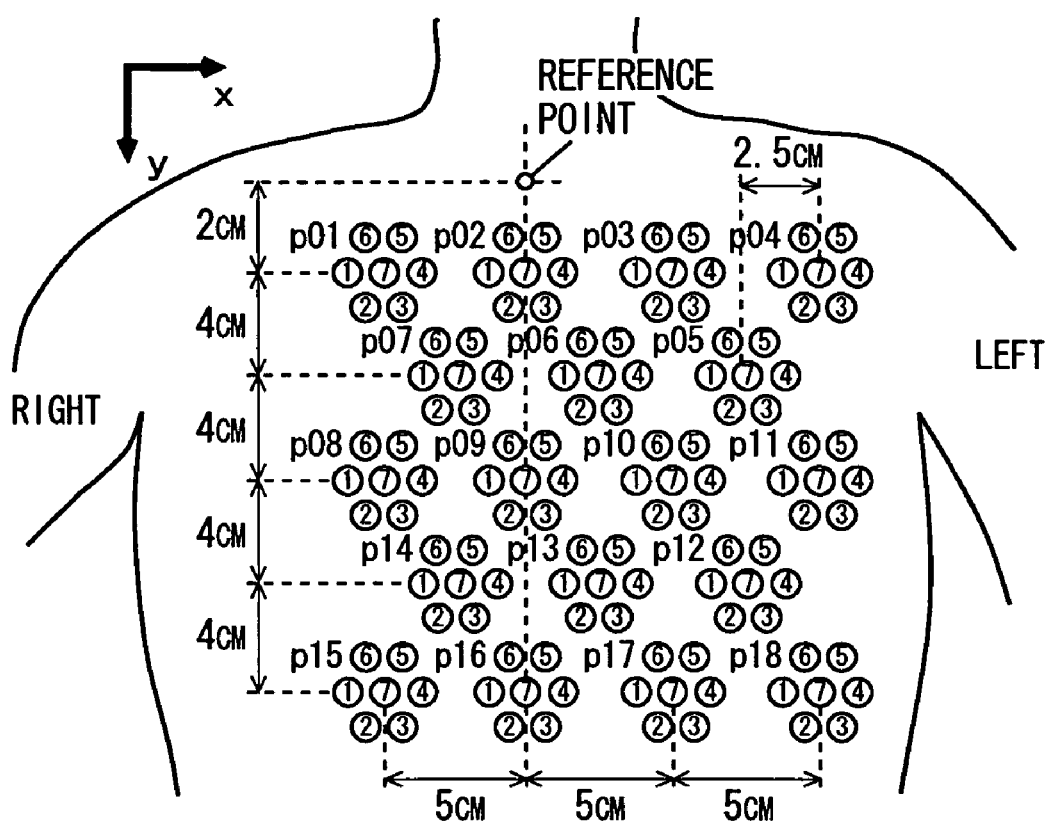
FIG. 4 shows by way of example an arrangement of a plurality of magnetic field sensors on a front side of the chest of a subject.

FIG. 4 exemplarily shows an arrangement of a plurality of sensors (each corresponding to a SQUID magnetometer of a single channel) on a front side of the chest of a subject. Furthermore, FIG. 5 represents a group of time-series magnetic field data representing a variation of a magnetic field for the period of a single heart beat that is obtained from the respective sensors of FIG. 4, as corresponding to their respective positions.

Figure 5:
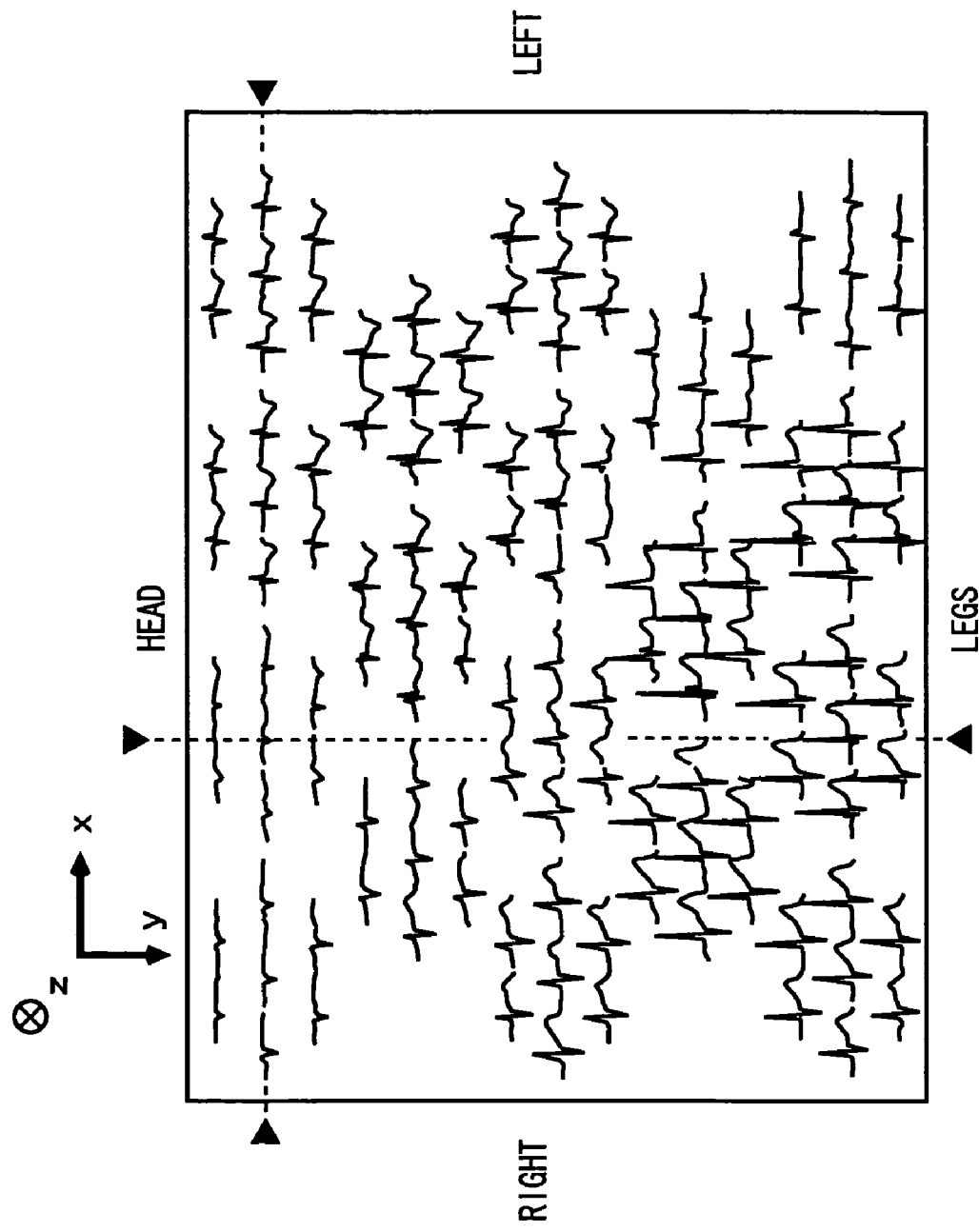
FIG. 5 represents time-series magnetic field data obtained from the plurality of sensors shown in FIG. 4, respectively.

Magnetic field distribution measurement device 1 shown in FIG. 2 outputs a group of time-series magnetic field data corresponding to a plurality of positions (coordinates) for measurement, as shown in FIG. 5. If a group of time-series magnetic field data is captured with a particular time noted, it is difficult to graphically (diagrammatically) represent ridges and troughs representing a distribution in intensity of a magnetic field present at a specific time on a front side of a chest to be measured, and magnetic field distribution data represented in a contour map such as an atmospheric pressure represented in a weather chart is accordingly obtained. In this sense also, data output from magnetic field distribution measurement device 1 can be captured as time-series data of a distribution of a magnetic field on a front side of a chest.

A group of time-series, magnetic field data such as output from magnetic field distribution measurement device 1, i.e., time-series magnetic field distribution data are fed to the first arithmetic device 2 of FIG. 2. The first arithmetic device 2 functions to obtain from magnetic field distribution data of a specific time an electrical behavior of that instant in the chest, e.g., a density of a current in the chest that flows at that instant.

From the time-series magnetic field distribution data generated by magnetic field distribution measurement device 1 the first arithmetic device 2 obtains three-dimensional information of an electrical behavior in a human body at a part to be measured (a heart in the present invention), e.g., a distribution of a density of a current flowing in a human body through the part of interest, as described hereinafter.

Figure 6:
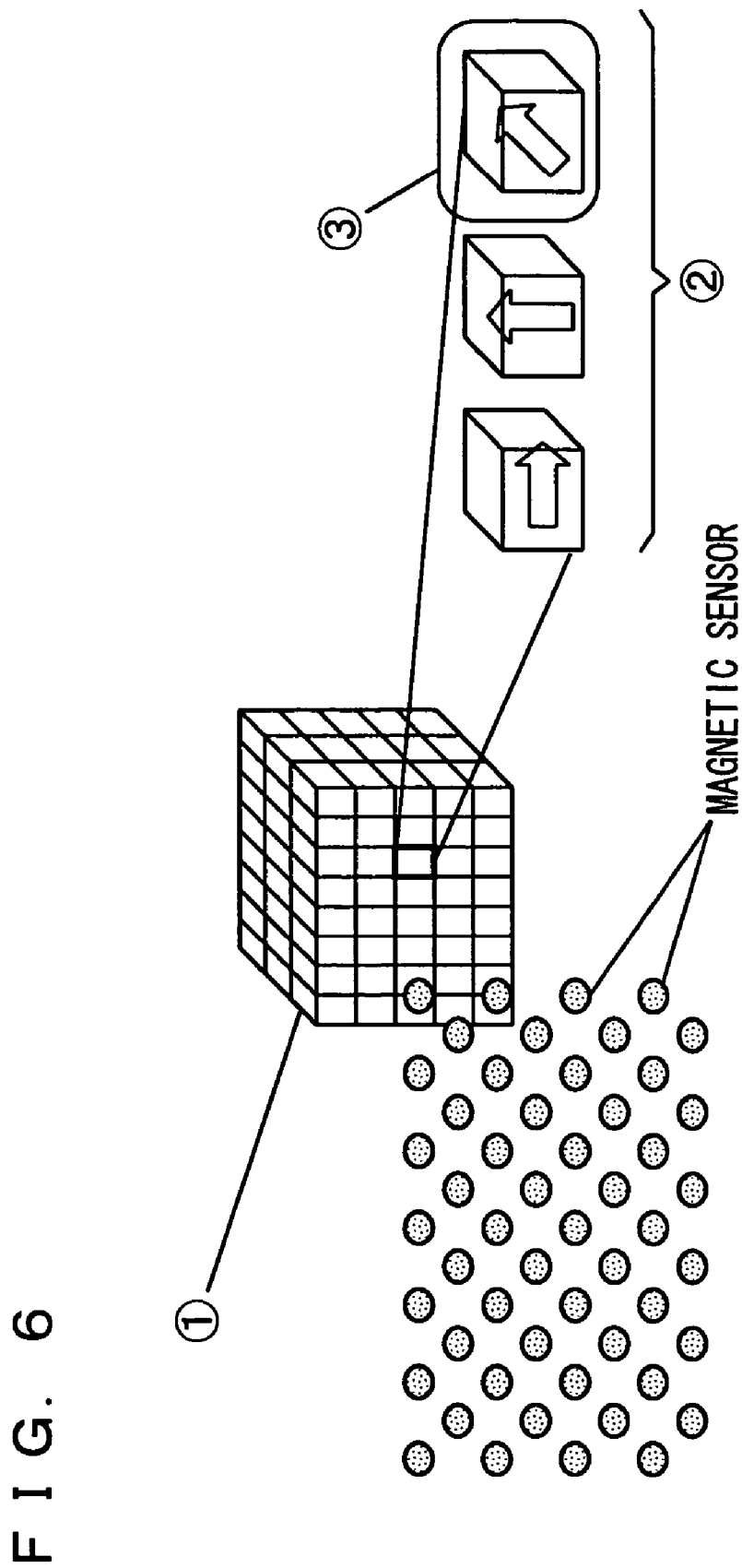
FIG. 6 schematically illustrates a method of calculating current density data from time-series magnetic field data.

FIG. 6 schematically illustrates a method of obtaining a current density. The method described hereinafter is intended to indirectly calculate a current that should flow through a virtual current sensor arranged at a specific single part of a human body to be analyzed. All of sensors (SQUID magnetometers) on the chest of a human body provide time-series magnetic field data, which can be multiplied by a coefficient and then added together to obtain an output of a current of the virtual sensor of interest. How the coefficient is obtained is a central issue in this arithmetic operation.

Hereinafter with reference to FIG. 6 a technique used to obtain a current density will be described more specifically. Initially on a surface of a human body (a front side of the chest thereof) there are arranged N magnetic field sensors in total for the sake of illustration. As indicated by a circled number of 1, a human body (a chest, a heart in particular) to be analyzed is regarded as a collection of voxels, each in the form of a small block. There are provided M voxels in total for the sake of illustration. As indicated by a circled number of 2, at a single coordinate there is arranged a voxel passing a distribution current of mutually orthogonal components, although a component orthogonal to a plane, as indicated by a circled number of 3, is often omitted, since in magnetocardiography a magnetic field sensor is often arranged on a chest in a plane.

$B_j(t)$ represents time-series magnetic field data obtained from each sensor j and $\beta_{ij}$ represents a spatial filter factor of a voxel i corresponding to each sensor output $B_j(t)$.

If it is assumed that in voxel i there exist a virtual current sensor and $S_i(t)$ represents a virtual sensor output corresponding to a current density obtained from the virtual current sensor then $S_i(t)$ is defined by the following expression:

$$Si(t) = \sum_{j=1}^{N} \beta_{ij} \cdot B_j(t).$$

As such, if a spatial filter factor $\beta_{ij}$ is determined a current density in each voxel i can be obtained and a three-dimensional current density distribution can be obtained for the entirety of a subject to be analyzed.

Spatial filter factor $\beta_{ij}$ that is highly sensitive only to a distribution current of corresponding voxel i can be set by synthetic aperture magnetometry (SAM), multiple signal classification (MUSIC) or other similar, various techniques. SAM and MUSIC have been studied and developed for example in the fields of radar and sonar and are well known techniques. However, they have hitherto been unapplied to magnetocardiographic diagnosis.

A virtual sensor output of each voxel that is calculated in real time using a spatial filter factor obtained by SAM, MUSIC or any other similar technique, is an advantageously highly implemented real-time output.

SAM and MUSIC are well known techniques and the algorithms using these techniques to obtain a spatial filter factor are significantly complicated, and they will not be described specifically. SAM is specifically described by Robinson S E and Vrba J, "*Functional Neuroimaging by Synthetic Aperture Magnetometry (SAM)*" in Proceedings of the 11th International Conference on Biomagnetic field, "*Reent Advances in Biomagnetic field*," published by Tohoku University Press, 1999, pp. 302–305. MUSIC is specifically described by Hiroshi Hara and Shinya Kurishiro, "*Science of Cerebric Magnetic field-SQUID Measurement and Medical Applications*," published by Ohmsha, Jan. 25, 1997, pp. 117–119.

Thus the first arithmetic device 2 generates from magnetic field distribution data generated by magnetic field distribution measurement device 1 time-series data representing a three-dimensional current density distribution in a heart to be analyzed and feeds the time-series data to display device 4 at one input.

The second arithmetic device 3 shown in FIG. 2 receives image data of a plurality of sliced images (for example a dozen of such images obtained at a pitch of five millimeters) of the chest of the same subject that are taken using another tomographic analysis apparatus (not shown) such as MRI, x-ray CT, echocardiography or myocardial SPECT with an electrocardiography synchronization trigger applied.

The second arithmetic device 3 processes (interpolates) the data of the plurality of sliced images and subjects the data to three-dimensional, perspective conversion from a predetermined point of view to generate second data representing an anatomical image. Thus forming a three-dimensional, anatomical image from a plurality of sliced images is a well-known technique, for example as specifically disclosed in Japanese Patent Laying-Open No. 11-128224 and International Publication WO 98/15226, and will not be described specifically.

Thus the second arithmetic device 3 generates the second data representing a three-dimensional, anatomical image of the chest of the same subject in a vicinity of his/her heart and feeds the second data to display device 4 at the other input.

Display device 4 of FIG. 2 superimposes on a three-dimensional, anatomical image of a subject's chest based on the second data from the second arithmetic device 3 an image based on the first data from the first arithmetic device 2 and representing a three-dimensional, intramyocardial current density distribution.

Figure 7A:
FIGS. 7A and 7B show an example of a three-dimensional, anatomical image displayed on a display device 4.
Figure 7B:

FIGS. 7A and 7B each show a manner of displaying in real time a three-dimensional current density distribution superimposed on a three dimensional, anatomical image displayed by display device 4. The figures show the current density distribution chronologically varying as time elapses.

FIGS. 7A and 7B each show a three-dimensional image obtained by interpolating approximately five tomographic images obtained for example by slicing a subject's chest at a pitch of five millimeters. An actually displayed image's depth is difficult to represent by drawing. In each of FIGS. 7A and 7B, a drawing configuring each image is represented by a plurality of superimposed drawings. As such, it can thus be determined to be a perspective, stereoscopic, anatomical image formed by combining a plurality of sliced images.

Note that FIGS. 7A and 7B each show a tomographic image with an upper portion corresponding to a front side of a human body and a lower portion to a back side thereof. Furthermore FIGS. 7A and 7B each show the tomographic image, as seen upward (at the legs).

In each of FIGS. 7A and 7B, a set of circles, as indicated by A, represents a three-dimensional current density distribution superimposed on a three-dimensional, anatomical image, and each circle's radius represents a magnitude of a current density. Alternatively, the magnitude of the current density can be represented by a tone of a specific color on a screen.

Figure 8:
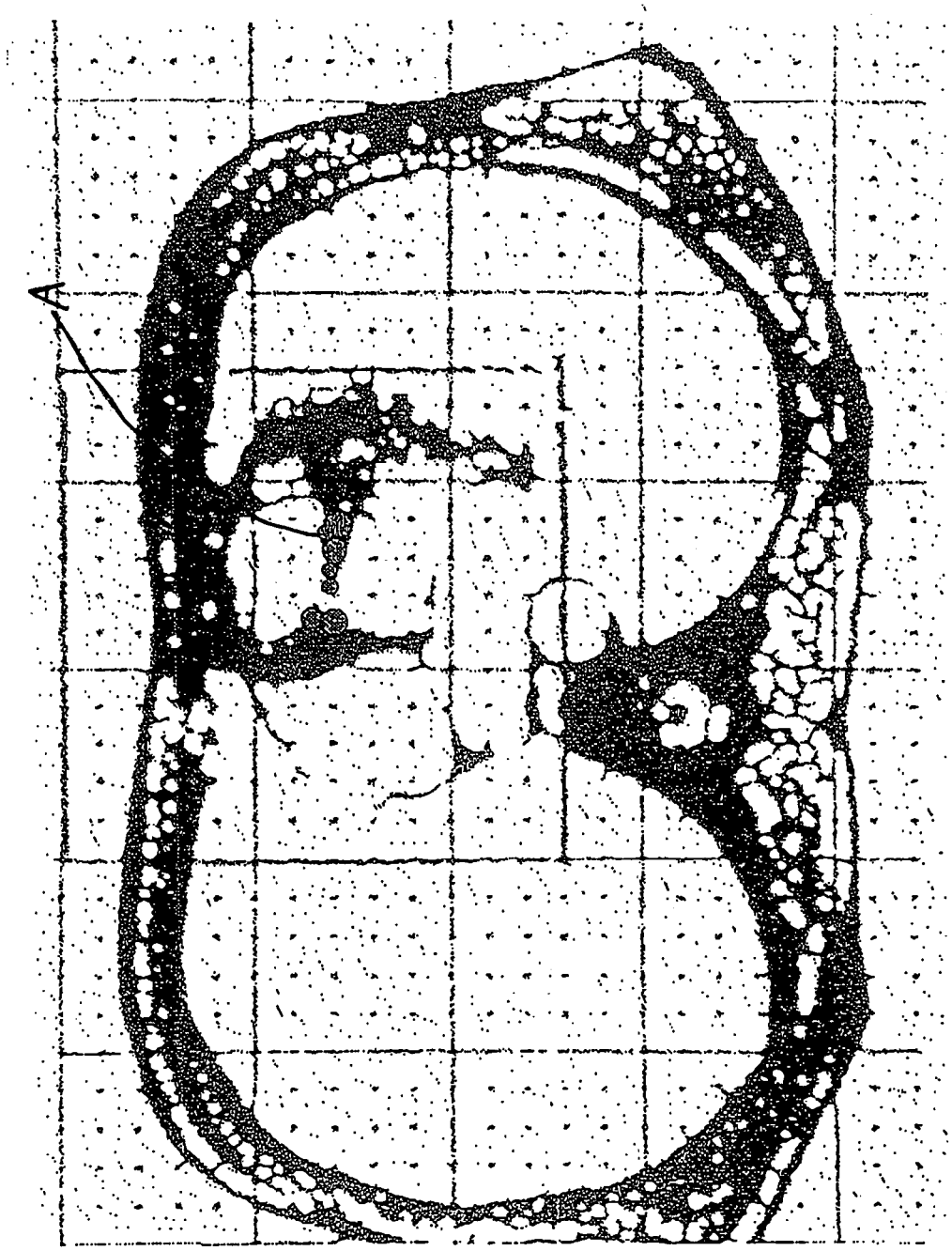
FIG. 8 tomographically shows a cross section of the image shown in FIGS. 7A and 7B.

Furthermore, FIG. 8 displays an extracted tomographic image obtained at a depth of such a perspective, stereoscopic, anatomical image as shown in FIGS. 7A and 7B, with a set of circles, similarly as indicated by A, representing a current density distribution on the tomographic image.

The perspective, three-dimensional, anatomical image with the three-dimensional, intramyocardial current density distribution displayed thereon allows a doctor to correctly understand a relative, positional relationship of the intramyocardial current density distribution on the anatomical image. In particular, if a displayed current density distribution indicates a local reentry, the doctor can correctly diagnose the location, size and geometry of an affected part in a heart muscle having an electrical reentry circuit that might cause atrial flutter and fibrillation.

Figure 9:
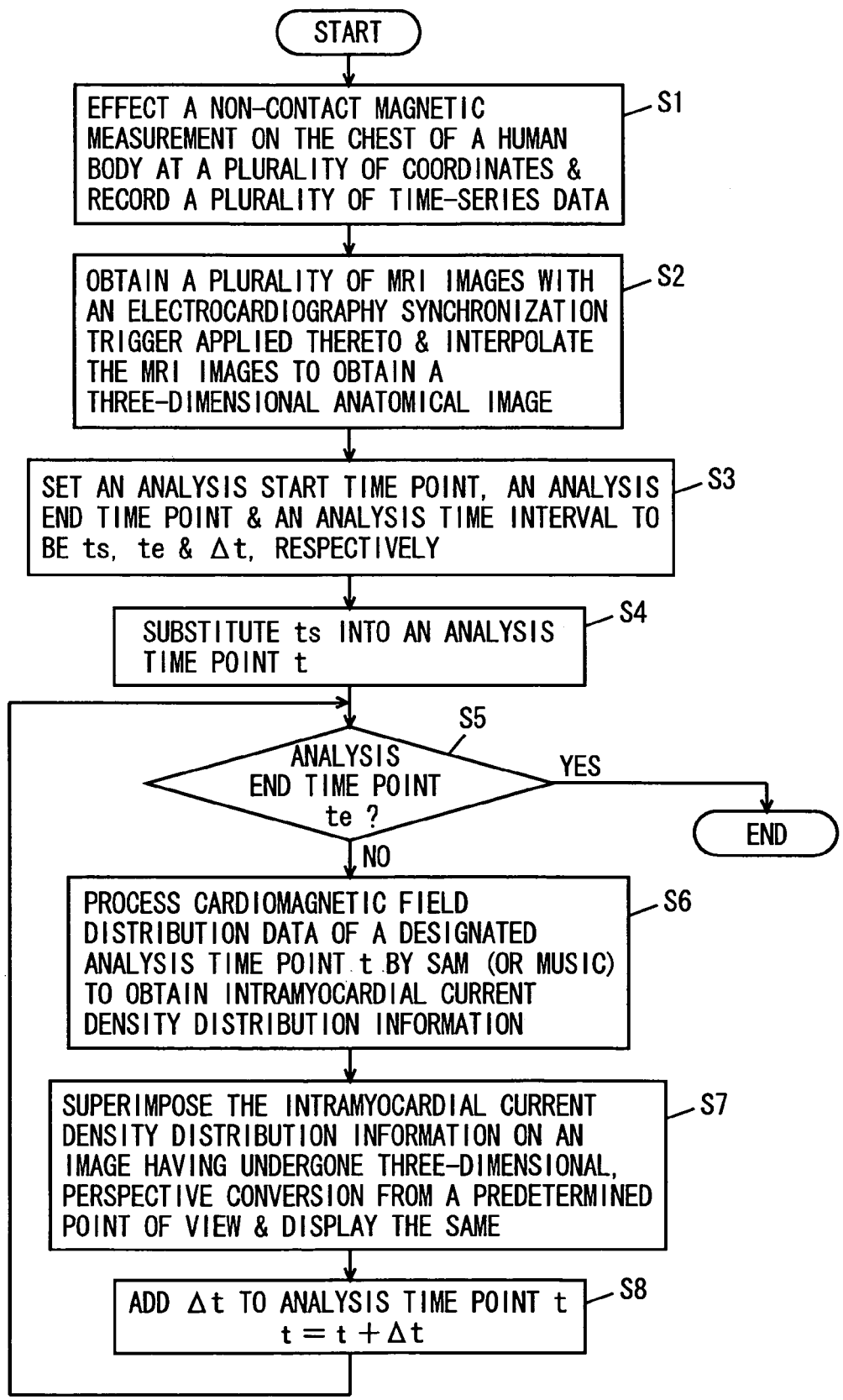
FIG. 9 is a flow chart for illustrating an operation of the magnetocardiographic diagnosis apparatus of the first embodiment.

FIG. 9 is a flow chart representing a method effected by the magnetocardiographic diagnosis apparatus of the first embodiment to identify an intramyocardial current density distribution (an abnormal, electrical reentry circuit in particular).

In FIG. 9 initially at step S1 magnetic field distribution measurement device 1 is used to provide non-contact magnetic field measurement on the chest of a human body at a plurality of coordinates, generate a plurality of time series data, and record the data if necessary. Note that the arithmetic operation/operations performed by the first arithmetic device 2 using SAM or MUSIC as aforementioned is/are performable on time-series data supplied in real time.

Then at step S2 a plurality of MRI images taken with an electrocardiography synchronization trigger applied are interpolated by the second arithmetic device 3 (i.e., subjected to three-dimensional, perspective conversion from a predetermined point of view) to obtain a three-dimensional, anatomical image.

Then at step S3 an analysis start time point, an analysis end time point and an analysis time interval are set to be $t_s$, $t_e$ and $\Delta t$, respectively.

Then at step S4 analysis start time point $t_s$ is substituted into an analysis time point t to start an analysis. Then at step S5 until analysis time point t reaches analysis end time point $t_e$ the following process is effected.

More specifically at step S6 the first arithmetic device 2 uses SAM or MUSIC to process magnetocardiographic distribution data corresponding to a designated analysis time point t and obtain intramyocardial current density distribution data.

Then at step S7 display device 4 superimposes the intramyocardial current density distribution data on the anatomical image having been subjected to three-dimensional, perspective conversion from the predetermined point of view and displays the same.

Then at step S8 $\Delta t$ is added to analysis time point t.

Steps S6–S8 are repeated until a decision is made at step S5 that analysis time point t has reached analysis end time point $t_e$. When it reaches analysis end time point $t_e$ display device 4 terminates displaying the intramyocardial current density distribution data superimposed on the anatomical image.

Thus in the first embodiment an image representing an intramyocardial current density distribution obtained from a SQUID magnetometer obtaining a noninvasive magnetic field measurement on a subject's chest can be superimposed on a three-dimensional, anatomical image and thus displayed to allow a doctor to three-dimensionally identify the anatomical, positional relationship, size and geometry of an abnormal, intramyocardial excitation propagation circuit, i.e., an electrical reentry circuit that might cause atrial flutter and fibrillation.

As such in thoracotomy a multi-point, simultaneous, myocardial potential measurement can be dispensed with to identify safely, rapidly and with high precision an abnormal excitation propagation circuit that might cause atrial flutter and fibrillation. Thoracotomy can thus be performed in a significantly reduced period of time and a burden on patients can be alleviated.

Furthermore, it is no longer necessary to conduct an electrophysiological test using a catheter while effecting chest x-ray fluoroscopy, as performed in a conventional diagnosis, to identify an abnormal excitation propagation circuit safely, rapidly and with high precision, as described above. As such, doctors and radiographers can be free from significantly long periods of time of x-ray exposure. A burden on doctor and radiographers can thus be alleviated.

Furthermore the method of identifying an electrical reentry circuit in the first embodiment can be used together with high frequency catheter cauterization to allow a less invasive surgical operation to be employed to treat atrial flutter and fibrillation and thus further reduce a burden on patients.

Furthermore, in the present embodiment, as data representing an intramyocardial, electrical behavior a current density distribution can be measured. As such, a diagnosis can be made while consistency between an intramyocardial current density distribution and a medical finding about survival myocardium can readily be established.

Second Embodiment

In the first embodiment, forming an anatomical image entails obtaining a large number of tomographic images of a subject and a test employing MRI, x-ray CT or the like is accordingly, previously conducted. This results in an increased number of tests and an increased burden on patients and also an obstacle to a treatment directly linked to a test.

The present invention in a second embodiment can provide a magnetocardiographic diagnosis apparatus and a method of identifying an electrical reentry circuit, capable of eliminating the formation of an anatomical image to conduct a reduced number of tests and carry out a diagnosis and a test such that they are directly linked.

Figure 10:
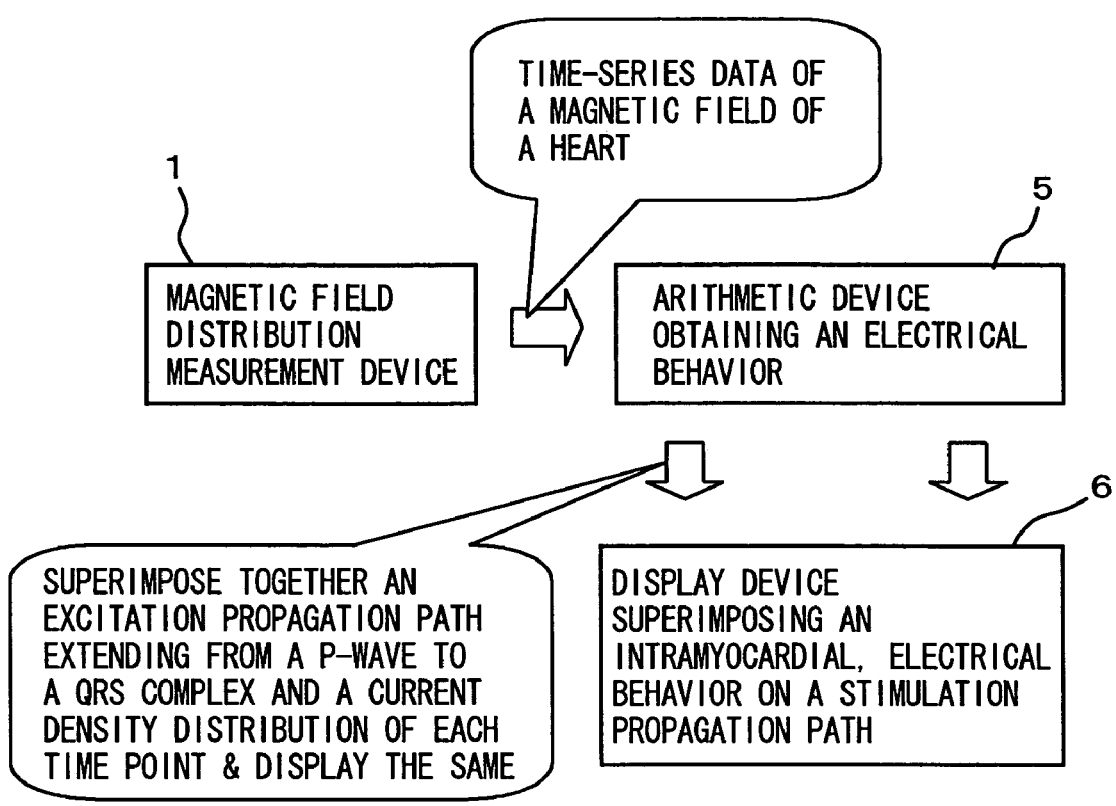
FIG. 10 is a functional block diagram schematically showing a configuration of a magnetocardiographic diagnosis apparatus for atrial flutter and fibrillation in accordance with the present invention in a second embodiment.

FIG. 10 is a functional block diagram schematically showing a configuration of the magnetocardiographic diagnosis apparatus for atrial flutter and fibrillation in the second embodiment.

With reference to FIG. 10, magnetic field distribution measurement device 1 will not be described as it has been described in the first embodiment.

Magnetic field distribution measurement device 1 generates time-series, magnetic field distribution data and outputs the data to an arithmetic device 5 which in turn uses the received time-series, magnetic field distribution data and employs the aforementioned SAM, MUSIC or any other similar calculation technique to generate data representing an intramyocardial, three-dimensional electrical behavior, e.g., a three-dimensional current density distribution. Arithmetic device 5 then uses the generated three-dimensional current density distribution data to superimpose data representing an intracardiac excitation (stimulation) propagation path of a period corresponding to that from an electrocardiographically represented P wave to an electrocardiographically represented QRS complex and data representing a current density distribution on each other and outputs the same to display device 6.

Display device 6 superimposes an image representing the intramyocardial current density distribution represented by the data generated by arithmetic device 5, on a three-dimensional image of the excitation propagation path also obtained by arithmetic device 5 and corresponding to the period from the P wave to the QRS complex, and displays the same. Consequently, such an anatomical image as used in the first embodiment can be dispensed with to three-dimensionally identify a positional relationship of an intramyocardial, electrical reentry circuit.

Figure 11:
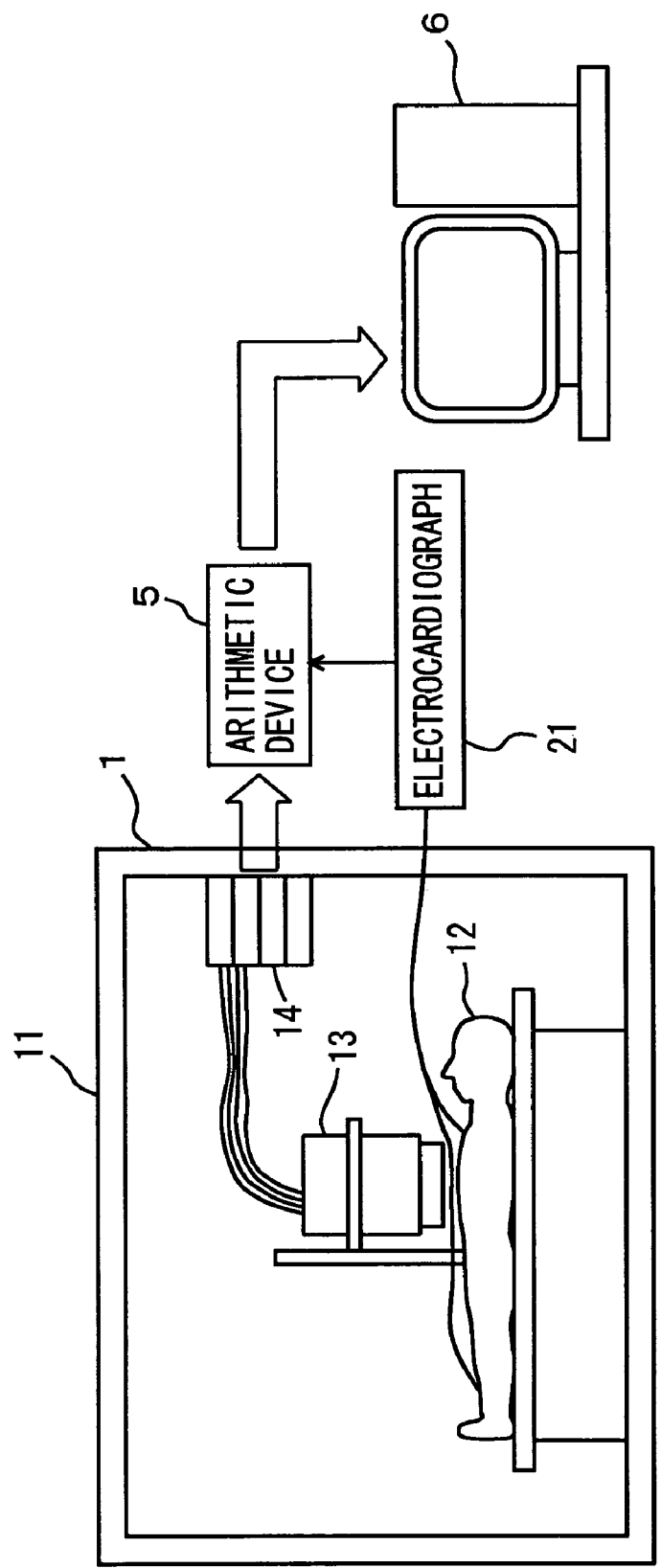
FIG. 11 is a block diagram more specifically showing the configuration of the FIG. 10 apparatus.

FIG. 11 is a block diagram more specifically showing a configuration of the magnetocardiographic diagnosis apparatus of the second embodiment shown in FIG. 10.

With reference to FIG. 11, magnetic field distribution measurement apparatus 1 will not be described as it is identical to that described with reference to FIGS. 2 and 3.

Magnetic field distribution measurement device 1 outputs time-series, magnetic field distribution data and outputs the data to arithmetic device 5 shown in FIG. 11. Arithmetic device 5 uses SAM, MUSIC or any other similar technique, as described with reference to FIG. 6, to convert the time-series, magnetic field distribution data to time-series, current density distribution data.

Subject 12 has his/her electrocardiogram recorded by an electrocardiograph 21 to allow measured electrocardiographic waveform data of subject 12 to be fed to arithmetic device 5.

Note herein that if the electrocardiographically represented waveform and a generated current density distribution can be correlated, the electrocardiogram and an event occurring in the heart can also be correlated.

Figure 12A:
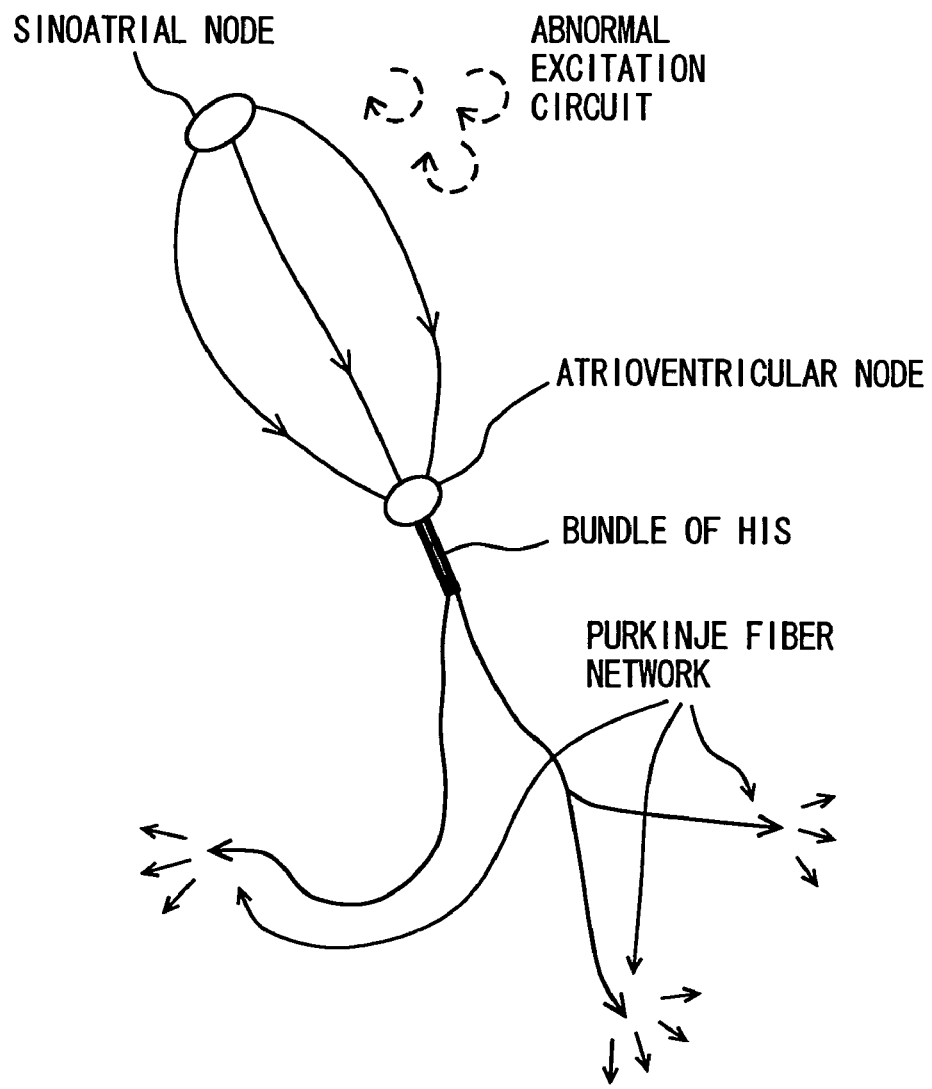
FIGS. 12A and 12B schematically show a normal stimulation propagation path in a heart and an electrocardiographically represented waveform.
Figure 12B:
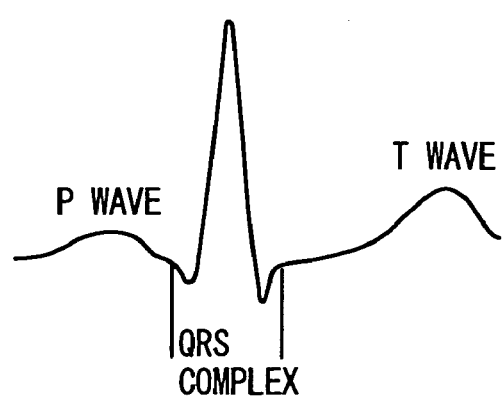

Reference will now be made to FIG. 12A schematically representing a normal stimulation propagation path in a heart and FIG. 12B representing an electrocardiographically represented waveform for a single heart beat.

With reference to FIGS. 12A and 12B, a sinoatrial node functions as a pacemaker determining a heart beat and it fires at predetermined intervals (a timing of a P wave of an electrocardiogram) to generate a pulse. This pulse is transmitted through a specific stimulation propagation path to an atrioventricular node and therein after a period of time elapses a pulse is transmitted through a bundle of His and a Purkinje fiber network to an underlying a ventricle and myocardial contraction erupts. This propagation of a stimulation from the bundle of His to the Purkinje fiber network corresponds to the period of the QRS complex in the electrocardiogram (an isovolumetric contraction time).

As such, by analyzing magnetocardiographic related to the period from the P wave to the QRS complex, i.e., an intramyocardial current density distribution, arithmetic device 5 generates image data representing a stimulation propagation path serving as a normal route, as shown in FIG. 12A.

An image of a stimulation propagation path, such as shown in FIG. 12A, can be used in place of the anatomical image used in the first embodiment, as a template displayed. More specifically, a three-dimensional, anatomical image such as described in the first embodiment can be dispensed with if a stimulation propagation path of a normal route, as shown in FIG. 12A, is displayed, since an abnormal excitation circuit caused in a vicinity thereof, for example an abnormal, electrical reentry circuit, indicated in FIG. 12A by a broken line, would be readily, anatomically correlated and its location, size and geometry would be identified by doctors.

Arithmetic device 5 shown in FIG. 11 generates data representing a generated current density distribution, superimposed on a displaying of a stimulation propagation circuit as a template, such as described above. As has been described previously, noting a local reentry of an image representing a current density distribution allows an abnormal excitation circuit, i.e., an electrical reentry circuit to be found, and such image data can be combined with the aforementioned template image data and fed to display device 6.

Display device 6 shown in FIG. 11 uses the data received from arithmetic device 5 to display an image representing a current density distribution, as superimposed on a normal stimulation propagation circuit serving as a template.

Figure 13:
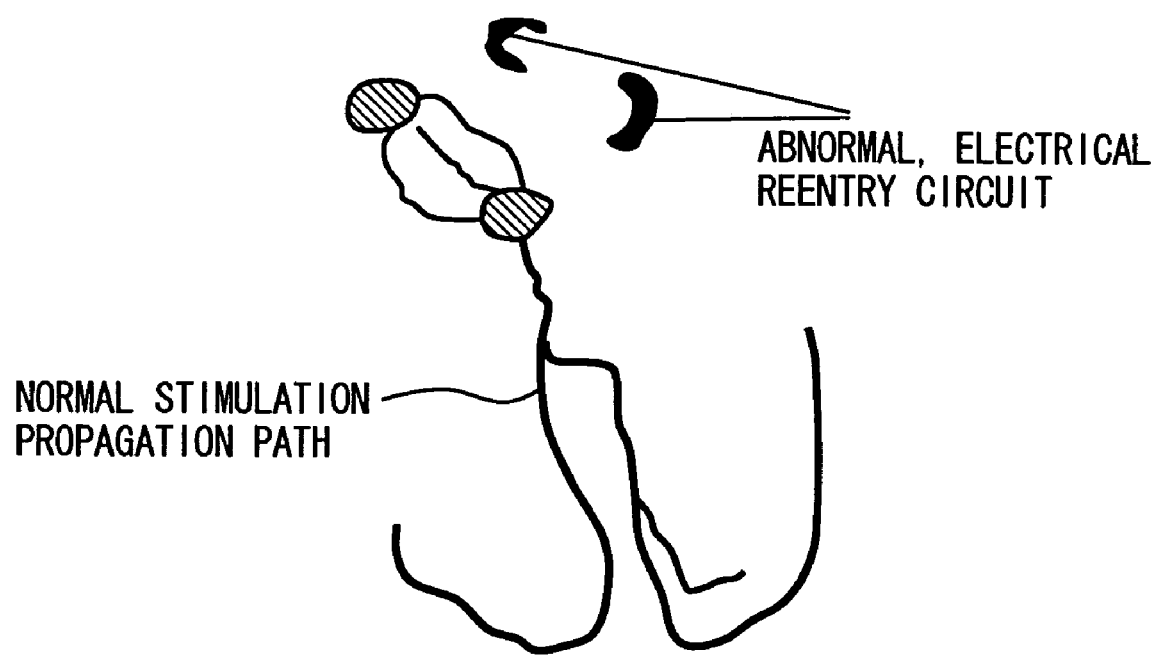
FIG. 13 shows an image of a normal stimulation propagation path and an abnormal, electrical reentry circuit, as displayed by display device 6.

FIG. 13 exemplarily shows a screen actually displayed by display device 6. It displays an image of a current density distribution representing an abnormal, electrical reentry circuit, superimposed on a normal stimulation propagation circuit serving as a template.

A doctor would be able to use solely a positional relationship of the electrical reentry circuit relative to the normal stimulation propagation circuit serving as a template, as shown in FIG. 13, to readily provide an anatomical correlation and identify the electrical reentry circuit in location, size and geometry.

Figure 14:
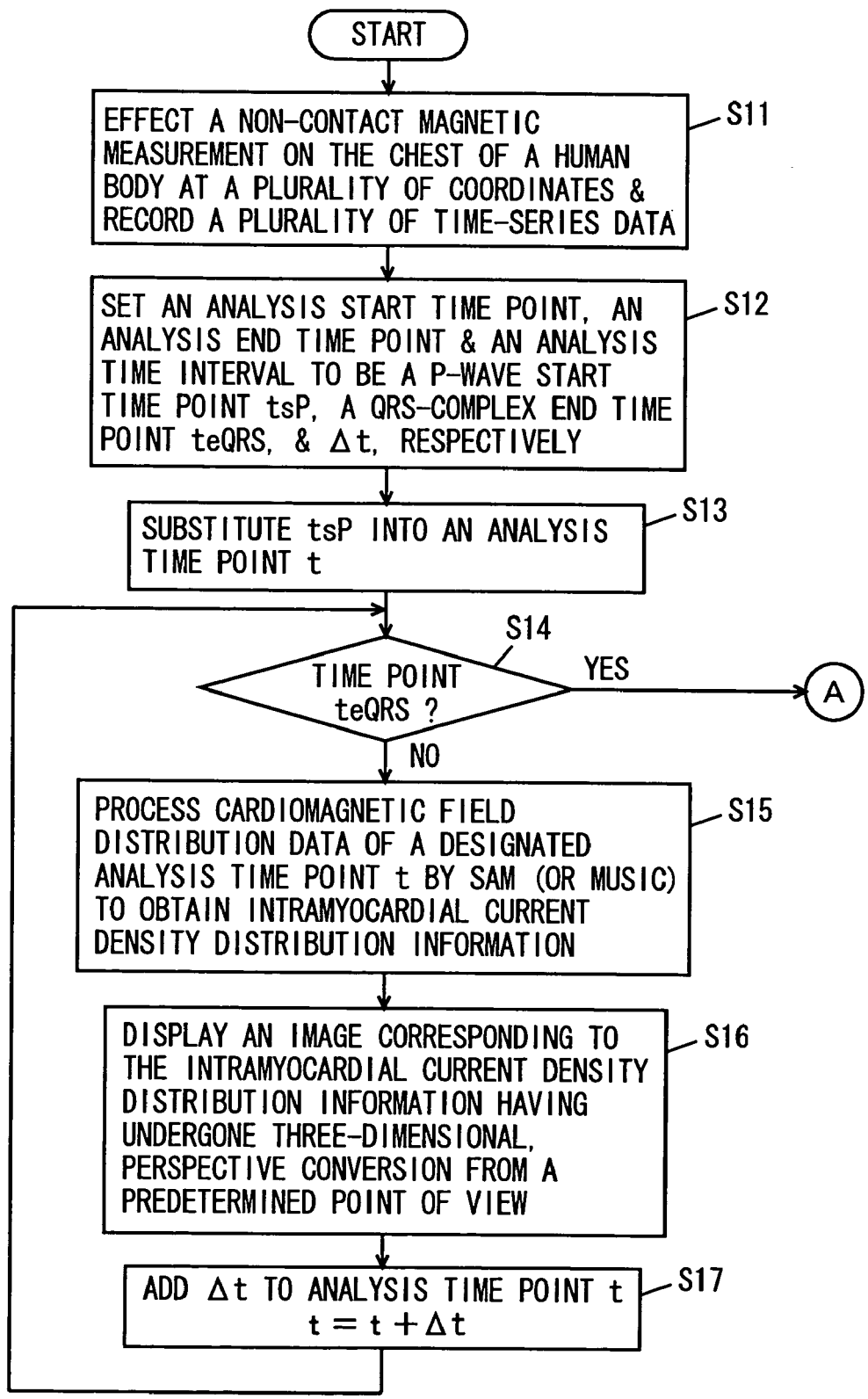

FIGS. 14 and 15 are a flow chart representing a method effected by the magnetocardiographic diagnosis apparatus of the second embodiment to identify an intramyocardial current reentry circuit.

Initially, with reference to FIG. 14, at step S11 magnetic field distribution measurement device 1 is used to provide a non-contact magnetic field measurement on the chest of a human body at a plurality of coordinates to generate and record a plurality of time-series magnetic field data.

Then at step S12 an analysis start time point is set to correspond to an electrocardiographically represented P-wave start time point $t_sP$, an analysis end time point to an electrocardiographically represented QRS-complex end time point $t_eQRS$, and an analysis time interval to $\Delta t$.

Then at step S13 time point $t_sP$ is substituted into analysis time point t.

Then at step S14 until an analysis time reaches time point $t_eQRS$ the following steps S15–S17 are repeated.

More specifically at step S15 arithmetic device 5 uses SAM or MUSIC to process magnetocardiographic distribution data of a designated analysis time point t to generate intramyocardial current density distribution data.

Then at step S16 the intramyocardial current density distribution data having been subjected to three-dimensional, perspective conversion from a predetermined point of view is displayed in an image.

Then at step S17 $\Delta t$ is added to analysis time point t and the process returns to step S14 and a decision is made as to whether time point $t_eQRS$ has been reached. If so then it means that there has been obtained image data representing a stimulation propagation path corresponding to a normal route, as shown in FIG. 12A, as corresponding in an electrocardiographically represented waveform to the period from the P wave to the QRS complex.

Then the process proceeds with step S18, shown in FIG. 15, and an analysis start time point, an analysis end time point and an analysis time interval are set to be $t_s$, $t_e$ and $\Delta t$, respectively.

Then at step S19 analysis start time point $t_s$ is substituted into analysis time point t.

Then at step S20 until a decision is made that analysis time point t has reached analysis end time point $t_e$ the following steps S21–S23 are effected.

More specifically, at step S21 arithmetic device 5 uses SAM or MUSIC to process magnetocardiographic distribution data of a designated analysis time point t to generate intramyocardial current density distribution data.

Then at step S22 the intramyocardial current density data is superimposed on an image of a normal stimulation propagation circuit having been subjected to three-dimensional, perspective conversion from a predetermined point of view, and it is thus displayed.

Furthermore at step S23 $\Delta t$ is added to analysis time point t and the process returns to step S20 and a decision is made as to whether analysis end time point $t_e$ has been reached. Thus, data representing the intramyocardial current density distribution is superimposed on an image of a normal stimulation propagation path (FIG. 12A) obtained through the FIG. 14 flow chart, and it is thus displayed.

Thus in the second embodiment an image representing an intramyocardial current density distribution obtained from a SQUID magnetometer obtaining a noninvasive magnetic field measurement on a subject's chest can be superimposed on a normal stimulation propagation path serving as a template and it can thus be displayed to eliminate the necessity of superimposing it on an anatomical image to allow a doctor to three-dimensionally identify the positional relationship, size and geometry of an abnormal, intramyocardial excitation propagation circuit that might cause atrial flutter and fibrillation, i.e., an electrical entry circuit relative to a stimulation propagation circuit. As such the second embodiment can eliminate the necessity of previously conducting a test to obtain an anatomical image.

Furthermore, if a catheter is used to conduct a test and provide a treatment while chest x-ray fluoroscopy is provided, as conventional, the second embodiment also allows an abnormal, intramyocardial excitation propagation circuit to be identified safety, rapidly and with high precision, as described above. Accordingly, doctors and radiographers can be free from significantly long period of time of x-ray exposure. A burden on doctors and radiographers can thus be alleviated.

Furthermore a test for creating an anatomical image can be dispensed with. As such, by using the method of identifying an electrical reentry circuit, as described in the second embodiment, together with high frequency catheter cauterization a treatment directly linked to diagnosis of atrial flutter and fibrillation can be provided and a burden on patients can further be alleviated.

Furthermore, in the second embodiment, as data representing an intramyocardial, electrical behavior a current density distribution can be measured. As such, a diagnosis can be made while consistency between an intramyocardial current density distribution and a medical finding about survival myocardium can readily be established.

Thus in accordance with the present invention an intramyocardial, electrical behavior obtained through a noninvasive magnetic field measurement on a patient's chest can be displayed visibly on a three-dimensional, anatomical image to three-dimensionally identify an abnormal, intramyocardial, electrical reentry circuit in location, geometry and number.

As such, doctors and radiographers conducting an electrophysiological test using a catheter while chest x-ray fluoroscopy is provided can be free from significantly long periods of time of annual x-ray exposure and thoracotomy can be performed in a significantly reduced period of time. As a result, both a burden on patients and that on doctors can be alleviated.

Furthermore, also introducing the present invention before a treatment employing high frequency catheter cauterization allows diagnosis to be conducted efficiently.

In particular, if data representing an electrical behavior generated is current density distribution data, a current density distribution of an abnormal, intramyocardial excitation propagation circuit generated and an intramyocardial current density distribution can be readily correlated. As such, if different numbers are set or different initial values are used, they do not disadvantageously result in different results, as provided in a conventional analysis methodology using one or more current dipoles to mimic the source of a magnetic field.

In accordance with the present invention in still another aspect a subject's abnormal, electrical reentry circuit can be superimposed on the same subject's normal stimulation propagation circuit from a sinoatrial node to a bundle of His and a Purkinje fiber network to eliminate the necessity of obtaining an anatomical image to three-dimensionally identify an abnormal, intramyocardial, electrical reentry circuit in location, size, geometry and number. In other words, a test conducted to obtain an anatomical image can be eliminated to provide effectively increased efficiency in economy.

INDUSTRIAL APPLICABILITY

Thus in accordance with the present invention a magnetocardiographic diagnosis apparatus for atrial flutter and fibrillation and a method of identifying an electrical reentry circuit for atrial flutter and fibrillation can three-dimensionally identify an abnormal, intramyocardial, electrical reentry circuit in location, geometry and number and thus useful in conducting an electrophysiological test using a catheter while providing chest x-ray fluoroscopy or in providing a treatment employing high frequency catheter ablation.

The invention claimed is:

1. A magnetocardiographic diagnosis apparatus for atrial flutter and fibrillation, comprising:
    a magnetic field distribution measurement device (1) performing a non-contact magnetic field measurement on a subject's chest at a plurality of coordinates to obtain a plurality of time-series magnetic field data corresponding to said plurality of coordinates, and also using said plurality of time-series magnetic field data to generate time-series magnetic field distribution data on said chest;
    an arithmetic device (5) using said generated time-series magnetic field distribution data to generate data representative of a three-dimensional, intramyocardial, electrical behavior of said subject; and
    a display device (6) using the data generated by said arithmetic device to superimpose together an image representing a stimulation propagation path of said subject extending from a sinoatrial node to a bundle of His-Purkinje fiber network and an image representing an abnormal, intramyocardial, electrical reentry circuit and display said images, thereby capable of three-dimensionally identifying an abnormal, intramyocardial, electrical reentry circuit.

2. The apparatus of claim 1, wherein said data generated by said arithmetic device and representative of said three-dimensional, intramyocardial, electrical behavior is intramyocardial, time-series current density distribution data and wherein said display device three-dimensionally displays a location of a plurality of abnormal, electrical reentry circuits on said image of said stimulation propagation path, as based on said time-series current density distribution data.

3. A method of identifying an electrical reentry circuit for atrial flutter and fibrillation, comprising the steps of:
    performing a non-contact magnetic field measurement on a subject's chest at a plurality of coordinates to obtain a plurality of time-series magnetic field data corresponding to said plurality of coordinates and used to generate time-series magnetic field distribution data of said chest and generating first data representative of a three-dimensional, intramyocardial, electrical behavior of said subject from the generated time-series magnetic field distribution data;
    processing separately fed, tomographic, thoracic image data of said subject to generate second data representative of an anatomical image; and
    displaying an image of said three-dimensional, intramyocardial, electrical behavior represented by said first data, as superimposed on said anatomical image represented by said second data, to permit an abnormal, intramyocardial, electrical reentry circuit to be three-dimensionally identified.

4. The method of claim 3, wherein said three-dimensional, intramyocardial, electrical behavior represented by said first data is an intramyocardial current density distribution.

5. A method of identifying an electrical reentry circuit for atrial flutter and fibrillation, comprising the steps of:
    performing a non-contact magnetic field measurement on a subject's chest at a plurality of coordinates to obtain a plurality of time-series magnetic field data corresponding to said plurality of coordinates and used to generate time-series magnetic field distribution data of said chest and generating data representative of a three-dimensional, intramyocardial, electrical behavior of said subject from the generated time-series magnetic field distribution data; and
    using said generated data to superimpose together an image representing a stimulation propagation path of said subject extending from a sinoatrial node to a bundle of His-Purkinje fiber network and an image representing an abnormal, intramyocardial, electrical reentry circuit, and thus displaying said images to allow said abnormal, intramyocardial, electrical reentry circuit to be three-dimensionally identified.

6. The method of claim 5, wherein said three-dimensional, intramyocardial, electrical behavior represented by said data is an intramyocardial current density distribution.

* * * * *

UNITED STATES PATENT AND TRADEMARK OFFICE
CERTIFICATE OF CORRECTION

| | |
|---|---|
| PATENT NO. | : 7,123,952 B2 |
| APPLICATION NO. | : 10/333023 |
| DATED | : October 17, 2006 |
| INVENTOR(S) | : Kenji Nakai et al. |

It is certified that error appears in the above-identified patent and that said Letters Patent is hereby corrected as shown below:

On the Title Page,
Item (30) Foreign Application Priority Data

" Jul. 18, 2000 (JP).....................2001-217833"

Should read:
-- Jul. 18, 2000 (JP).....................2000-217833--

Signed and Sealed this

Twenty-sixth Day of June, 2007

JON W. DUDAS
*Director of the United States Patent and Trademark Office*